United States Patent [19]

Barton et al.

[11] 4,159,326

[45] Jun. 26, 1979

[54] HYDROGENATION PROCESS FOR THE PREPARATION OF 5,6 CIS- AND 5,6-TRANS-10,19-DIHYDRO-VITAMIN D COMPOUNDS USING TRANSISTION METAL CATALYSTS

[75] Inventors: Derek H. R. Barton, London, England; Robert H. Hesse, Cambridge, Mass.

[73] Assignee: Research Institute for Medicine & Chemistry, Inc., Cambridge, Mass.

[21] Appl. No.: 801,825

[22] Filed: May 31, 1977

[30] Foreign Application Priority Data

Jun. 3, 1976 [GB] United Kingdom ............... 23036/76

[51] Int. Cl.² ............................................ A61K 31/59
[52] U.S. Cl. .................................. 424/236; 260/397.2
[58] Field of Search ...................... 260/397.2; 424/236

[56] References Cited

U.S. PATENT DOCUMENTS

| | | | |
|---|---|---|---|
| 2,942,009 | 6/1960 | Westerhof | 260/397.2 |
| 3,049,553 | 8/1962 | Schenck | 260/397.2 |
| 3,607,888 | 9/1971 | DeLuca et al. | 260/397.2 |
| 3,697,559 | 10/1972 | DeLuca et al. | 260/397.2 |
| 3,725,489 | 4/1973 | Fuhrmann et al. | 260/397.2 X |
| 4,011,250 | 3/1977 | Ishikawa | 260/397.2 |

*Primary Examiner*—Ethel G. Love
*Attorney, Agent, or Firm*—Bacon & Thomas

[57] ABSTRACT

A process for the preparation of 5,6-cis- and 5,6-trans-10,19-dihydro-vitamin D derivatives which comprises hydrogenating a corresponding vitamin D compound in the presence of a ligand-coordinated homogeneous transition metal catalyst whereby the C-19 methylene group of the vitamin D compound is converted into a methyl group.

15 Claims, No Drawings

HYDROGENATION PROCESS FOR THE PREPARATION OF 5,6 CIS- AND 5,6-TRANS-10,19-DIHYDRO-VITAMIN D COMPOUNDS USING TRANSISTION METAL CATALYSTS

The present invention relates to a process for the preparation of 10,19-dihydro-5,6-trans-vitamin D compounds (i.e. 9,10-dihydrotachysterol compounds) and the corresponding 5,6-cis-isomers (i.e. 10,19-dihydro-vitamin D compounds).

10,19-Dihydro-vitamin D compounds are closely related to vitamin D compounds, having a methyl group in place of the methylene group at C-19 in the vitamins, and are useful in medicine for a variety of purposes including for example, the maintenance of serum calcium in hypoparathyroidism, the prophylaxis of rickets, and the treatment of renal osteodystrophy, osteoporosis and similar vitamin D responsive diseases. In general, they are more stable and less susceptible to oxidation than the vitamin D compounds themselves.

However, the preparation of such 10,19-dihydro-vitamin compounds has, in the past, proved difficult since previous processes have tended to produce isomeric mixtures which are difficult to separate. Thus, for example, attempts to reduce selectively the C-19 methylene groups of vitamin D compounds with conventional catalysts such as an Adams catalyst or platinum or palladium on charcoal, have resulted in mixtures of isomers in which other double bonds have been reduced, as well as cis-trans-isomerism about the 5,6-double bond. Reduction of the triene system with dissolving metals in amines, while useful for the commercial preparation of dihydrotachysterol, also affords mixtures of other dihydro vitamin D isomers. Furthermore both methods give fairly poor yields when applied to 1α-hydroxy vitamin D compounds, described for example in British Pat. No. 1,463,985 since hydrogenation of the C-19 methylene grouping also results to some extent in the reductive removal of the 1α-hydroxy group.

It is an object of the present invention to provide a new and advantageous process for the preparation of 10,19-dihydro-vitamin D compounds in either the 5,6-trans- or 5,6-cis-configuration.

We have found that vitamin D compounds can be readily converted into the corresponding 10,19-dihydro-vitamin D compounds by hydrogenating the vitamin D compounds in the presence of a ligand-coordinated homogeneous transition metal catalyst. The 10,19-dihydro-vitamin D derivatives can thus be readily obtained in good yield from the relatively accessible vitamin D compounds.

According to a preferred feature of the present invention we provide a process for the preparation of 5,6-cis- and 5,6-trans-10,19-dihydro-vitamin D derivatives which comprises hydrogenating a corresponding vitamin D compound in the presence of a ligand-coordinated homogeneous transition metal catalyst whereby the C-19 methylene group of the vitamin D compound is converted into a methyl group.

The metal component of the catalyst employed in the above-described process is advantageously selected from group VIII of the Periodic Table, rhodium and ruthenium being preferred. The metal is conveniently employed in the form of a salt thereof, e.g. a halide such as the chloride. The transition metal is advantageously coordinated with tri-substituted phosphine ligands, the substituent groups on the phosphine molecule preferably being alkyl (e.g. $C_{1-8}$) groups and/or aromatic (e.g. phenyl) groups which may, if desired, be substituted. Triphenylphosphine is preferred as a ligand, the transition metal advantageously being coordinated with 3 molecules of this ligand per atom of metal. A particularly preferred catalyst for use in the process according to the invention is tris-(triphenylphosphine) rhodium chloride.

The hydrogenation is generally effected in a solvent medium comprising, for example, one or more organic solvents e.g. hydrocarbons such as benzene and/or alkanols such as ethanol. The hydrogenation may be conveniently effected at ambient temperature.

The process described above is applicable to the preparation of not only the 10,19-dihydro-5,6-trans-vitamin D derivatives (i.e. 9,10-dihydrotachysterol derivative) but also the corresponding 5,6-cis-derivatives. The 10,19-dihydro-vitamin D derivatives which may be prepared by the new process preferably have a 17-side chain of formula

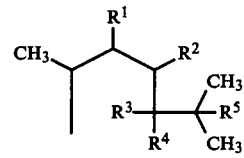

wherein $R^1$ and $R^2$, which may be the same or different, each represent hydrogen atoms or hydroxy or protected hydroxy groups or together form a carbon-carbon bond or an epoxy group, $R^3$ and $R^5$, which may be the same or different, each represent a hydrogen atom or a hydroxy or protected hydroxy group, and $R^4$ represents a hydrogen atom or a methyl or ethyl group.

The 10,19-dihydro-vitamin D compounds which may be prepared by the new process may thus, for example, be represented by the formula

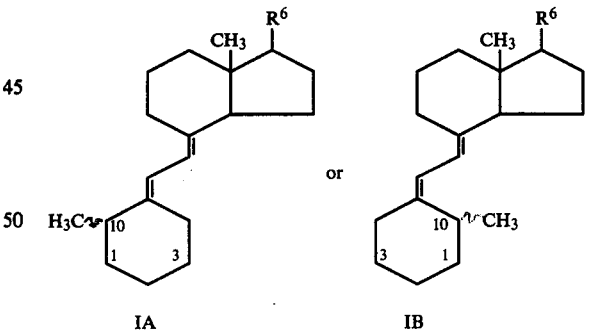

(wherein $R^6$ represents the above-identified 17-side chain).

The compounds of formula IA and IB may carry further ring substituents, and in general will carry at the 3-position a hydroxy or protected hydroxy group. The compounds may carry at the 1-position a hydroxy or protected hydroxy group, preferably in the α-configuration. Protected hydroxy groups present in the molecule may, for example, be acyloxy groups (e.g. alkanoyloxy groups having 1-6 carbon atoms or aroyloxy groups having 7-10 carbon atoms such as acetoxy or benzoyloxy groups) or ether groups (e.g. silyloxy groups such as trimethylsilyloxy groups).

Although such protected forms are in general physiologically active, the free hydroxy forms are preferred for use in medicine. Where a hydroxyl-protected vitamin is hydrogenated, the protecting groups may thus be deprotected subsequently e.g. by conventional methods. Thus, acyloxy groups may be removed by basic hydrolysis, e.g. with alkali metal alkoxide in an alkanol. Silyloxy groups may be removed by acid hydrolysis.

Formulae IA and IB above represent the 5,6-trans and 5,6-cis forms respectively.

The new process is especially useful for the preparation of 10,19-dihydro-5,6-cis and 5,6-trans-vitamins $D_2$ and $D_3$ and their 1α-hydroxy-substituted and 1α, 25-dihydroxy-substituted derivatives.

The hydrogenation of a 5,6-cis vitamin D compound in accordance with the above process may result in an isomeric mixture of 10,19-dihydro-vitamin D compounds comprising for example, the anti-isomer and the syn-isomer (i.e. the corresponding epi-compound), such mixtures generally containing a major proportion of the anti-compound. The references to "syn" and "anti" in the present specification are intended to denote the relative configuration of the 3-hydroxy and 19-methyl groups. Similarly, the hydrogenation of 5,6-trans vitamin D compound may also result in an isomeric mixture of syn- and anti-compounds, the latter compound (9,10-dihydrotachysterol) generally forming a major proportion of the mixture. Thus, for example, the hydrogenation of vitamin $D_3$ (5,6 cis-) in accordance with the invention may result in a mixture of compounds of formulae.

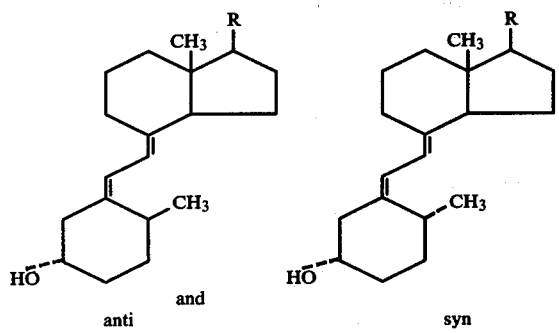

anti         and         syn while the hydrogenation of 5,6-trans- vitamin $D_3$ may result in a mixture of compounds of formulae

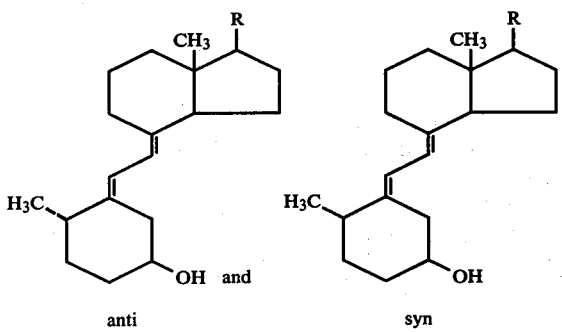

anti         and         syn the group R in the above formulae being the vitamin $D_3$ 17-side chain.

Similarly, the hydrogenation of 1α-hydroxy-vitamin $D_3$ (5,6-cis) in accordance with the invention may result in a mixture of compounds of formulae

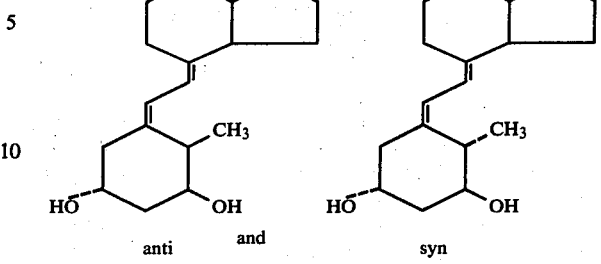

anti         and         syn while the hydrogenation of 5,6-trans 1α-hydroxy vitamin $D_3$ may result in a mixture of compounds of formula

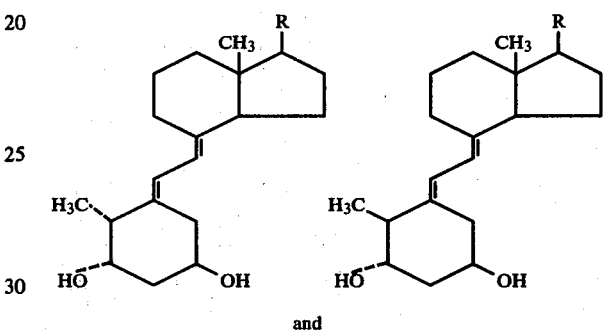

and the group R in the above formula being the vitamin $D_3$ 17-side chain,

The 1- and 3-hydroxyl groups in the above formulae may be protected, e.g. as acetoxy groups; where the anti-isomer is required, however, we have found it preferably to use the unprotected 1α-hydroxy vitamin D. The hydrogenation catalyst appears to form a complex with the 1-hydroxyl group and leads to a much slower reaction than if the 1-hydroxyl is protected but to a more stereospecific reduction to the anti isomer. This finding does not extend to the 1-desoxy compounds.

If desired, the mixtures of epimers which may be obtained by the above process can be separated in conventional manner, e.g. by chromatography. However, if desired, mixtures of syn- and anti-compounds can be employed as such in medical or veterinary applications where individual isolated isomers are not essential.

The process according to the invention is particularly applicable to the preparation of the anti-epimer of 1α-hydroxy-10,19-dihydro-5,6-trans vitamin $D_3$ the latter epimer being obtainable in a relatively high yield in comparison with the corresponding syn-epimer.

When a 10,19-dihydro-5,6-trans-vitamin D compound (i.e. a 9,10-dihydrotachysterol compound) is desired, the corresponding 5,6-trans-vitamin D compound, employed as starting material, may be prepared, for example, by isomerising the corresponding 5,6-cis-vitamin D compound, e.g. by treatment in iodine, preferably in an organic solvent such as hexane.

The following specific compounds are new and constitute further features of the present invention, namely:
(1) syn- and anti- epimers of 10,19-dihydro-5,6-cis-1α-hydroxy - vitamin $D_3$, syn-epimer of 10,19-dihydro-5,6-trans-1α-hydroxy-vitamin $D_3$ and mixtures of one or more of such analogues (2) syn- and anti-epimers of 10,19-dihydro-5,6-cis- and 5,6-trans - 1α, 25-dihydroxy-vitamin D₃ and mixtures of one or more of such analogues.

The syn-epimer of 1α-hydroxy-10,19-dihydro-5,6-cis-vitamin D₃ has been found in tests on rats to provide a particularly rapid increase in serum calcium levels which renders the compound of particular value in medical therapy for the treatment of vitamin D disorders.

The invention particularly extends to such compounds when separated from hydrogenated vitamin D compounds wherein double bonds other than the C-19 methylene group have been reduced.

The above new compounds and mixtures have been found to have important practical advantages over the corresponding vitamin D compounds in that they tend to be more stable, less susceptible to oxidation and less sensitive to acid-catalysed allylic dehydration.

The above new compounds and mixtures thereof possess vitamin D-like activity and thus constitute an important new class of biologically active materials capable of, inter alia, stimulating intestinal calcium transport, bone calcium mobilisation, bone mineralisation and bone formation, and pharmaceutical compositions containing effective amounts of one or more of these compounds or a mixture thereof and methods of treatment in human and veterinary medicine involving their administration comprise features of the present invention.

The new compounds and mixtures thereof, in particular those having a hydroxyl group in the 1α-position have important prophylactic and therapeutic applications in the prevention or treatment of disorders such as rickets and osteomalacia and are of value in the treatment of both vitamin D responsive and vitamin D resistant diseases such as hypoparathyroidism, hypophosphataemia, hypocalcaemia and/or associated bone disease, renal disorders or renal failure and hypocalcaemic tetany. Furthermore, the activity of the new compounds and mixtures, and their rapid onset and termination of activity similar to that of 1α-hydroxy-vitamin D₃, renders them of value where vitamin D should be avoided because of its cumulative toxicity and, in particular, in the treatment of disorders such as vitamin D resistant rickets, renal osteodystrophy, steatorrhea, biliary cirrhosis and other malfunctions of absorption, osteoporosis, secondary hypocalcaemia and/or bone disease arising from dysfunction of the liver, kidneys or gastrointestinal tract, and secondary hypocalcaemia, osteoporosis or other bone diseases resulting from treatment with steroids, such as corticoids, diphenylhydantoin, barbiturates such as phenylbarbitone, and related drugs, which prove refractory to conventional compounds such as vitamin D₃.

In general the new compounds and mixtures thereof may be administered parenterally in combination with an injectable liquid carrier such as sterile pyrogen-free water, sterile peroxide-free ethyl oleate, dehydrated alcohol, propylene glycol or a dehydrated alcohol/propylene glycol mixture. Such compositions may be injected intravenously, intraperitoneally or intramuscularly. Injectable compositions are preferably prepared in dosage unit form, e.g. in ampoules, each unit advantageously containing 0.02 to 200 μg, preferably 0.1-200 μg, advantageously containing 0.02 to 20 μg of the active ingredient; the syn- (i.e. epi-) compounds generally require 2- to 3- times the dose of the corresponding anti-compounds. The normal dosage for adult human treatment will generally be in the range 0.02 to 200 μg, preferably 0.1-200 μg per day, lower dosages within this range, e.g. 0.02 to 5 μg, preferably 0.1-2 μg being used in prophylaxis and higher dosages, e.g. 5-50 μg being used in some therapeutic applications.

If desired, the above pharmaceutical compositions may contain an antioxidant such as ascorbic acid, butylated hydroxyanisole, butylated hydroxytoluene or hydroquinone.

The new compounds and mixtures thereof may, for example, be used as food supplements or components of food supplements, e.g. in combination with other vitamins. Such food supplements or components thereof may contain for example, mixtures of the new 10,19-dihydro-vitamin D derivatives e.g. epimeric mixtures of 10,19-dihydro analogues of 5,6-trans- and/or 5,6-cis 1α-hydroxy or 1α, 25-dihydroxy-vitamin D₃.

The new compounds or mixtures may, if desired, also be presented in orally administrable pharmaceutical compositions for a wide range of applications, e.g. the treatment of any of the above-mentioned vitamin D responsive or, alternatively, any of the 1α-hydroxy vitamin D responsive - conventional vitamin D refractory diseases, particularly the long-term treatment of diseases such as osteoporosis, and prophylactic applications such as vitamin and multi-vitamin preparations.

Orally administrable compositions containing the new compounds may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions are preferably prepared in dosage unit form, each unit advantageously containing 0.02 to 20 μg, preferably 0.2 μg, more preferably 0.5-5 μg of new compound. Tablets and capsules containing the new compounds may, if desired, contain conventional ingredients such as binding agents, for example syrup, acacia, gelatin, sorbitol, tragacanth or polyvinyl-pyrrolidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats, emulsifying agents, for example lecithin, sorbitan monooleate or acacia; non-aqueous vehicles, which may include edible oils, for example vegetable oils such as arachis oil, almond oil, fractionated coconut oil, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

The compositions of the invention may contain other therapeutically useful ingredients such as calcium salts (e.g. the lactate, sodium lactate, phosphate, gluconate or hypophosphite) and/or salts of other essential trace elements such as magnesium, manganese, iron, copper, zinc and iodine and/or other vitamins such as vitamin A, vitamin $B_1$, vitamin $B_2$, nicotinamide, pantothenic acid or salts thereof e.g. the calcium salt, vitamin $B_6$, vitamin $B_{12}$ folic acid, vitamin C and vitamin E. Multivitamin preparations incorporating the new compounds may be formulated in an analogous manner to such vitamin preparations employing conventional 1-hydrogen vitamin D compounds. Depending upon their intended mode of use, the compositions may also contain, for example, a steroid (e.g. an anti-inflammatory steroid) such as prednisolone or betamethasone or an estrogen (e.g. methylstilbestrol, 17α-ethynyl estradiol, estrone, estradiol, estriol and conjugated equine. estrogens)

The activity of the new compounds also renders the compounds suitable for rectal administration, and pharmaceutical compositions for this purpose, e.g. containing an effective dose of the new compounds in admixture with a conventional suppository base such as cocoa butter or another glyceride fall within the scope of the invention.

As indicated above, it may be advantageous to incorporate an antioxidant, for example ascorbic acid, butylated hydroxyanisole or hydroquinone in the compositions of the invention to enhance their storage life.

The following examples illustrate the present invention:

EXAMPLE 1: Hydrogenation of Vitamin $D_3$

A solution of tris (triphenylphosphine) rhodium chloride (925mg) in ethanol (35ml)/benzene (35ml) was stirred under hydrogen for 30 mins. Vitamin $D_3$ (384mgs) was then added and the hydrogenation continued for 140 mins. during which time approximately 1 mole of hydrogen was consumed by the substrate. The solvent was then removed under reduced pressure, the residue triturated with methylene chloride, filtered and the red insoluble filtrate washed two times with small amounts of methylene chloride. The combined filtrates were evaporated to dryness and chromatographed to give two products: the major product i.e. the anti-epimer of 10,19-dihydro-5,6-cis-vitamin $D_3$ (292mgs) was a pale yellow oil with $R_f$ slightly greater than that of starting material (vitamin). For characterisation this material was treated with para nitrobenzoyl chloride (200mgs) in dry pyridine (2 ml) for 48 hours. A further portion of 100 mgs of the acid chloride was added after 24 hours. Aqueous work up and chromatography afforded the para nitrobenzoate which crystallized from acetone/methanol, melting point 55°–60°. $UV\lambda_{max}$. ether 237 ($\epsilon$=32,300), 243 ($\epsilon$=42,500), 250.5 ($\epsilon$=47,500), 260 ($\epsilon$=34,200). Analysis: $C_{34}H_{49}NO_4$ Requires: C, 76.22; H, 9.22: N, 2.61; Found: C, 76.54; H, 9.18; N, 2.68%. The minor hydrogenation product i.e. the syn-epimer of 10,19-dihydro-5,6-cis-vitamin $D_3$ (71mgs) with a slightly lower $R_f$ than the vitamin was treated in the same way to give a para nitrobenzoate; melting point 143°–144.5°. $UV\lambda_{max}$. ether: 236.5 ($\epsilon$=30,200), 243 ($\epsilon$=43,000), 251 ($\epsilon$=53,200), 260.5 ($\epsilon$=43,600). Analysis: $C_{34}H_{49}NO_4$: Requires: C, 76.22; H, 9.22; N, 2.61%; Found: C, 76.46; H, 9.22; N, 2.76%.

EXAMPLE 2: Hydrogenation of 5,6-trans Vitamin $D_3$

To a solution of Vitamin $D_3$ (750 mgs) in hexane (20 ml) was added iodine (2 mgs). After stirring for 1 hr. at 20° the solution was washed with aqueous sodium thiosulphate, water and dried over sodium sulphate. After removal of the solvent, chromatography afforded trans-vitamin $D_3$ (460mgs).

A mixture of 5,6-trans-vitamin $D_3$ (400mgs) and tris (triphenylphosphine) rhodium chloride (1.0gms) in benzene (35ml)/ethanol (35ml) was hydrogenated as in Example 1. Following work up as in Example 1 the material was chromatographed to afford two products in approximately equal amounts. The less polar product i.e. the syn-epimer of 10,19-trans-vitamin $D_3$ (10 epi-dihydrotachysterol, 193 mgs.) had the following physical constants: $UV\lambda_{max}$. 242 (0.86), 250.5 (1.0), 260 (0.67), the figures in parenthesis being relative absorptions. Treatment of this with para nitrobenzoyl chloride as in Example 1 gave a para nitrobenzoate, melting point 45°–60°, solidified and remelted 79°–80°. Analysis: $C_{34}H_{49}NO_4$ Required: C, 76.22; H, 9.22; N, 2.61%; Found: C, 76.35; H, 9.06; 2.61%.

The second hydrogenation product which was identical in all respects to 9,10-dihydrotachysterol (i.e. the anti-epimer of 10,19-dihydro-5,6-trans-vitamin $D_3$) (203mgs) was slightly less polar than the parent vitamin.

EXAMPLE 3: Hydrogenation of 1α-Hydroxy Vitamin $D_3$ Diacetate

1α-Hydroxy vitamin $D_3$ diacetate (22mgs) in ethanol (4ml)/benzene (4ml)/containing tris (triphenylphosphine) rhodium chloride (42 mgs.) was hydrogenated as in Example 1. After work up as in Example 1 the residue was chromatographed on thin layer plates to afford two products as above. The major and more polar product (18.5 mgs) had $UV\lambda_{max}$. 236.5 (0.64), 342.5 (0.88), 251 (1.00), 260.5 (0.67). The minor product (4.2 mgs) had $UV\lambda_{max}$. 236 (0.66), 242 (0.88), 250.5 (1.00), 259.5 (0.68). The extinction coefficient of each at 251nm was approximately 40,000. The major and minor products were respectively the anti- and syn-epimers of 10,19-dihydro-1α-hydroxy-5,6-cis-vitamin $D_3$ diacetate. The major and minor products respectively were hydrolyzed to the free dihydro vitamin derivatives by treatment with 0.5% KOH in methanol at 20° for 2.5 hours.

EXAMPLE 4: Isomerization of 1α-Hydroxy vitamin $D_3$ to 5,6-trans- 1α-Hydroxy Vitamin $D_3$ Diacetate and Hydrogenation of the Same 1α-Hydroxy vitamin $D_3$ diacetate (55mgs) was treated with iodine in hexane in Example 2. Work up as in Example 2 afforded 5,6-trans- 1α-hydroxy vitamin $D_3$ diacetate (30mg) $\lambda_{max}$. 273nm. This material in ethanol (5ml)/benzene (5ml) containing tris (triphenylphosphine) rhodium chloride (60 mgs.) was hydrogenated as in Example 1. The major more polar product, 1α-hydroxy dihydrotachysterol diacetate (17 mgs), was separated from the minor less polar product, 10-epidihydro-1α-hydroxy dihydrotachysterol diacetate (10 mgs). Upon hydrolysis with KOH/methanol as above, the major diacetate afforded 1α-hydroxy 9,10-dihydrotachysterol (i.e. the anti-epimer of 10,19-dihydro-5,6-trans-1α-hydroxy vitamin $D_3$) melting point 175.5°–178°, $a_D+71°$ identical with authentic material. The minor product upon hydrolysis afforded 10-epi-1α-hydroxy-9,10-dihydrotachysterol (i.e. the syn-epimer of 10,19-dihydro-5,6-trans-1α-hydroxy-vitamin $D_3$ as a non-crystalline oil. UV $\lambda_{max}$. 237 (0.65) 243.5 (0.86), 251.5 (1.0) 261 (0.67).

EXAMPLE 5: Hydrogenation of 1α,25-Dihydroxy Vitamin D₃

A solution of 1α,25-dihydroxy vitamin D₃ (128 mgs) was treated with iodine as in Example 2. After 20 mins. at room temperature, the reaction was worked up as in Example 2. It was not possible to separate the cis- and trans- isomers of the vitamin by chromatography, however, crystallization from methylene chloride followed by two further crystallizations from ether afforded the 5,6-trans vitamin (22mgs), UVλ$_{max}$. 273nm. This material in ethanol (5ml)/benzene (5ml) containing tris (triphenylphosphine) rhodium chloride (1 mg) was hydrogenated as in Example 1. Work up as in Example 1 afforded the major more polar product 1α,25-dihydroxy 9,10-dihydrotachysterol (i.e. the anti-epimer of 10,19-dihydro-5,6-trans-1α-25-dihydroxy-vitamin D₃) together with a minor less polar product 1α,25-dihydroxy 10-epi-9,10-dihydrotachysterol (i.e. the syn-epimer of 10,19-dihydro-5,6-trans-1α,25-dihydroxy-vitamin D₃).

EXAMPLE 6: Hydrogenation of 5,6-trans-1α-hydroxy-vitamin D₃

5,6-trans-1α-hydroxy-vitamin D₃ (41mg) in benzene (8cc) and ethanol (8cc) containing tris-(triphenylphosphine)-rhodium chloride (1.05 molecular equivalents) was exposed to hydrogen overnight with stirring. Working up as in Example 1 yielded 35 mg of the anti-epimer of 10,19-dihydro-5,6-trans-1α-hydroxy-vitamin D₃ (1α-hydroxy-9,10-dihydrotachysterol) together with 8–14% of the syn-epimer.

The following Examples illustrate pharmaceutical or veterinary compositions according to the invention. Unless otherwise stated, references to 1α-hydroxy-10,19-dihydrovitamin D₃ and 1,25-dihydroxy-10,19-dihydro vitamin D₃ refer to any one of the syn- and anti-, cis- and trans-epimers or to mixtures thereof. Where 1α-hydroxy-10,19-dihydro vitamin D₃ is specified, thus can be replaced by 1,25-dihydroxy-10,19-dihydro vitamin D₃.

EXAMPLE 7

Orally Administrable Compositions (a) Capsules

1α-Hydroxy-10,19-dihydro vitamin D₃ is dissolved in sterile arachis oil of low peroxide containing 0.1% w/w butylated hydroxyanisole as antioxidant to give a solution with a vitamin concentration of 40 μg/ml. ¼ ml portions of the resulting solution are encapsulated in gelatin by conventional techniques.

Dose—1–2 capsules per day.

Capsules were also prepared by the above method solutions containing 2.0 μg/ml and 4.0 μg/ml respectively of the 1α-hydroxy-10,19-dihydro-vitamin D₃.

(b) Tri-vitamin preparation

Tablets comprising the following ingredients are prepared by conventional techniques:

| | |
|---|---|
| Vitamin A | 4000 u.s.p. units |
| Vitamin C | 75 mg |
| 1α-hydroxy-10,19-dihydro vitamin D₃ | 0.2–1 μg |

The preparation may optionally also contain 1 mg of fluorine as a physiologically compatible fluoride salt.

Dose—1 tablet per day.

(c) Deca-vitamin preparation (for adult use)

Tablets comprising the following ingredients are prepared by conventional techniques:

| | |
|---|---|
| Vitamin A | 25,000 u.s.p. units |
| Vitamin B₁ | 10 mg |
| Vitamin B₂ | 10 mg |
| Vitamin B₆ | 5 mg |
| Vitamin B₁₂ | 5 μg |
| Vitamin C | 200 mg |
| 1α-hydroxy-10,19-dihydro vitamin D₃ | 0.2–1 μg |
| Vitamin E | 15 I.U. |
| Calcium pantothenate | 20 mg |
| Nicotinamide | 100 mg |

The tablets may optionally also contain 1 mg of fluorine as a physiologically compatible fluoride salt and/or a mineral complex comprising the following elements in the form of physiologically compatible salts:

| | |
|---|---|
| Copper | 2 mg |
| Iodine | 0.15 |
| Iron | 12 mg |
| Magnesium | 65 mg |
| Manganese | 1 mg |
| Zinc | 1.5 mg |

Dose—1 tablet per day.

EXAMPLE 8

Feed Composition for Poultry

40 μg of 1α-hydroxy-10,19-dihydro-vitamin D₃ are dissolved in ethanol (100–500 ml) and the resulting solution is slurried with 2 kg of ground limestone. The ethanol is then removed under reduced pressure, with stirring of the slurry, and the resulting tachysterol-containing solid is added to poultry feed at a rate of 20 g per kilogram of feed.

If desired, a mixture of 10,19-dihydro-vitamin D compounds can be employed in the above-composition. Such mixtures may comprise for example a mixture of cis- and trans- compounds as well as epimeric mixtures of such compounds.

Feed compositions for cattle can be formulated in a similar manner to the above poultry feed.

EXAMPLE 9

Capsules

| | |
|---|---|
| 20 μg | 1α-hydroxy-10,19-dihydro-vitamin D₃ |
| 100 ml | Arachis oil |
| 100 mg | butyrated hydroxytoluene |
| 5 g | prednisolone USP micronised |

The above components are mixed in a high speed homogeniser and filled into 1000 0.1 ml gelatine capsules each containing 0.02 μg vitamin D₃ compound and 5 mg steroid. 1 to 4 capsules to be given daily.

Similar compositions may be prepared replacing the prednisolone by 0.6 g of betamethosone.

EXAMPLE 10

Capsules

| | |
|---|---|
| 20 μg | 1α-hydroxy-10,19-dihydro-vitamin D₃ |

| | |
|---|---|
| 100 ml | Arachis oil |
| 100 mg | butyrated hydroxytoluene |
| 20 mlg | 17α-ethynyloestradiol |

The above components are mixed in a high speed homogeniser and filled into 1000 0.1 ml gelatine capsules each containing 0.02 µg vitamin D₃ compound and 0.02 mg steroid. 1-3 capsules daily.

EXAMPLE 11

Capsules

Capsules were prepared as in Example 4 each containing:

| | |
|---|---|
| 0.25 µg | 1α-hydroxy-10,19-dihydro-vitamin D₃ |
| 0.25 mg | ethyl stilboestrol |
| 0.01 mg | butyrated hydroxy toluene |
| 0.1 ml | arachis oil |
| 1-4 capsules daily | |

EXAMPLE 12

Tablets 0.67 mg 1α-hydroxy-10,19-dihydro-vitamin D₃ and 0.1 g butyrated hydroxytoluene were dissolved in 5 ml ethanol and 5 g lactose added. Solvent was removed and the powder were mixed with

| | |
|---|---|
| 192.75 g | lactose |
| 1.0 g | stearic acid |
| 1.25 g | conjugated equine oestrogens USP | and compressed into 1000 200 mg tablets. 1-3 tablets per day.

We claim:

1. A process for the preparation of 5,6-cis- and 5,6-trans-10,19-dihydro-vitamin D derivatives which comprises hydrogenating a corresponding vitamin D compound in the presence of a ligand-coordinated homogeneous transition metal catalyst from group VIII of the Periodic Table coordinated with phosphine ligands tri-substituted by alkyl or aromatic groups, whereby the C-19 methylene group of vitamin D compound is converted into a methyl group.

2. The process of claim 1, wherein the alkyl group contains 1-8 carbon atoms and the aromatic group is a phenyl group.

3. A process as claimed in claim 1 wherein the said transition metal is rhodium or ruthenium.

4. A process as claimed in claim 1 wherein the said transition metal is employed in the form of a salt thereof.

5. A process as claimed in claim 1 wherein the said phosphine ligands are triphenylphosphine ligands.

6. A process as claimed in claim 1 wherein the said catalyst comprises tris-(triphenylphosphine)-rhodium chloride.

7. A process as claimed in claim 1 for the preparation of 5,6-cis- and 5,6-trans-10,19-dihydro-vitamin D derivatives having a 17-side chain of formula

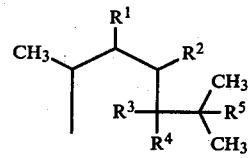

wherein R¹ and R², which may be the same or different, each represent hydrogen atoms or hydroxy or protected-hydroxy groups or together form a carbon-carbon bond or an epoxy group; R³ and R⁵, which may be the same or different, each represent a hydrogen atom or a hydroxy or protected-hydroxy group; and R⁴ represents a hydrogen atom or a methyl or ethyl group.

8. A process as claimed in claim 7 for the preparation of 5,6-cis- and 5,6-trans-10,19-dihydro-vitamin D derivatives containing a hydroxy or protected-hydroxy group in the 3-position.

9. A process as claimed in claim 7 for the preparation of 5,6-cis- and 5,6-trans-10,19-dihydro-vitamin D derivatives containing a hydroxy or protected-hydroxy group in the 1α-position.

10. A process as claimed in claim 8 for the preparation of 5,6-cis- and 5,6-trans-10,19-dihydro-vitamin D₃.

11. A process as claimed in claim 9 for the preparation of 5,6-cis- and 5,6-trans-10,19-dihydro-1α-hydroxy-vitamin D₃.

12. A process as claimed in claim 7 for the preparation of 5,6-cis- and 5,6-trans-10,19-dihydro-1α,25-dihydroxy-vitamin D₃.

13. A process as claimed in claim 1 in which the resulting vitamin D derivative comprises a mixture of syn- and anti-epimers which are subsequently separated.

14. A compound selected from the syn-epimer of 5,6-cis-10,19-dihydro-1α-hydroxy-vitamin D₃, the anti-epimer of 5,6cis-10,19-dihydro-1α-hydroxy-vitamin D₃, the syn-epimer of 5,6-trans-10,19-dihydro-1α-hydroxy-vitamin D₃, the anti-epimer of 5,6-trans-10,19-dihydro-1α-hydroxy-vitamin D₃, and the syn- and anti-epimers of 5,6-cis- and 5,6-trans-10,19-dihydro-1α,25-dihydroxy-vitamin D₃.

15. Pharmaceutical compositions comprising from 0.02 to 200 µg, as active ingredient, at least one compound as claimed in claim 14, in association with at least one pharmaceutical carrier or excipient.

* * * * *